United States Patent
Nørby et al.

(10) Patent No.: US 7,662,935 B2
(45) Date of Patent: Feb. 16, 2010

(54) PROCESSING OF PEPTIDES AND PROTEINS

(75) Inventors: Inga Sig Nielsen Nørby, Birkerød (DK); Lars Fogh Iversen, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/471,884

(22) Filed: May 26, 2009

(65) Prior Publication Data

US 2009/0253900 A1    Oct. 8, 2009

Related U.S. Application Data

(63) Continuation of application No. 12/177,539, filed on Jul. 22, 2008, now abandoned, which is a continuation of application No. 11/424,870, filed on Jun. 18, 2006, now abandoned, which is a continuation of application No. PCT/DK2004/000891, filed on Dec. 20, 2004.

(60) Provisional application No. 60/531,790, filed on Dec. 22, 2003, provisional application No. 60/539,290, filed on Jan. 26, 2004.

(30) Foreign Application Priority Data

Dec. 19, 2003   (DK) ............................. 2003 01892

(51) Int. Cl.
*A23J 1/00*    (2006.01)

(52) U.S. Cl. ...................................... 530/412; 435/220
(58) Field of Classification Search ................ 530/412; 435/220
See application file for complete search history.

(56) References Cited

U.S. PATENT DOCUMENTS 6,638,750 B1    10/2003   Aurora et al.

FOREIGN PATENT DOCUMENTS

WO    WO 99/61617    12/1999

OTHER PUBLICATIONS

Lowther, W T et al-Biochem Biophys Acta-2000-vol. 1477-pp. 157-167.
Chiu, C-H et al-J Bacteriol-1999-vol. 181-Part 15-pp. 4686-4689.
Walker, K W et al-The J of Biological Chem-1999-vol. 274-Part 19-pp. 13403-13409.
Lowther, W T et al—Bio Chem—1999—vol. 38—pp. 7678-7688.
Liao, Y-D et al—Protein Science—2004—vol. 13—pp. 1802-1810.
Liu, L—F et al—Anal Biochem—2004—vol. 329—pp. 345-347.
Sequence search alignment between Accession No. AAP70096 and Applicants' SEQ ID No. 3 [[EP219237 (1987), Benbassat et al.].

*Primary Examiner*—Tekchand Saidha
(74) *Attorney, Agent, or Firm*—Shelby Walker (57) ABSTRACT

The invention provides novel methionine aminopeptidase enzymes and their use.

4 Claims, 5 Drawing Sheets

FIG. 5

PROCESSING OF PEPTIDES AND PROTEINS

CROSS-REFERENCE TO RELATED PATENT APPLICATIONS

This patent application is a continuation of U.S. patent application Ser. No. 12/177,539, filed Jul. 22, 2008, now abandoned, which is a continuation of Ser. No. 11/424,870, filed Jun. 18, 2006, now abandoned, which is a continuation of International Application PCT/DK2004/000891, filed Dec. 20, 2004, which claims the benefit of U.S. Provisional Patent Application Nos. 60/531,790, filed Dec. 22, 2003 and 60/539,290, filed Jan. 26, 2004 and Danish Patent Application No. PA 2003 01892, filed Dec. 19, 2003.

FIELD OF THE INVENTION

The invention relates to a method for processing initiator methionine containing proteins by the enzyme Methionine Aminopeptidase and mutants thereof to yield initiator methionine free peptides.

BACKGROUND OF THE INVENTION

Production of peptides by recombinant techniques using either prokaryotic or eukaryotic expression systems inherently yields the peptide with a leading methionine amino acid. This amino acid may not be present in the native protein i.e. the variant of the peptide processed for translocation. Obtaining the peptide without the leading methionine thus requires a further processing step. In the present invention the step is performed by the enzyme Methionine Aminopeptidase, which selectively cleaves the initiator methionine from the peptide.

Methionine Aminopeptidases (Met-AP's) are known in the art as enzymes which cleaves leading methionines, if the leading peptide sequence is of a certain predetermined character. Wild-type *Escherichia coli* Met-AP selectively cleaves after an initiator Met residue if the residue in the P1' position is Gly, Ala, Ser, Thr, Pro, Val or Cys.

In the present invention the methionine aminopeptidases are improved by introducing mutations in the substrate binding sites which results in methionine aminopeptidases which cleaves the methionine regardless of the leading peptide sequence (P1' position)

SUMMARY OF THE INVENTION

The invention provides novel mutant methionine aminopeptidases.

The invention provides isolated DNA encoding such methionine aminopeptidases.

The invention provides host cells for producing such methionine aminopeptidases.

The invention provides the use of the mutant methionine aminopeptidase for processing of peptides with an initiator methionine amino acid into a methionine free peptide.

The invention also provides the processing of specific peptides by mutant methionine aminopeptidases.

The invention also provides a method for separating the methionine containing starting material from the final cleaved product.

DEFINITIONS

P1 defines the first amino acid N-terminal to the recognition site for the enzyme. P1' denotes the amino acid adjacent to P1 towards the C-terminal. P1 in the present invention is methionine.

In the present invention substrate specificity means selectivity towards the P1' position—which is the position just C-terminal to methionine. Wild-type *Escherichia coli* Met-AP exhibits the substrate specificity, that it selectively cleaves after an initiator Met residue if the residue in the P1' position is Gly, Ala, Ser, Thr, Pro, Val or Cys. The mutants of the present invention showing an extended substrate specificity means that further amino acid can occupy the P1' position and still cleavage of the methionine is observed.

In the context of the present invention variant means a sequence which has maintained the qualitative activity of the parent sequence, ie as methionine aminopeptidase, but wherein the sequence differs from the parent sequence by deletions, insertions, extension or substitution of one or more amino acids of the parent sequence. Variants in principle also includes fragments of any length provided the activity is maintained.

In the context of the present invention chemical derivatives of a specific protein means a derivative of the native protein which is not a variant, and which maintains the qualitative activity of the parent protein sequence. The chemical derivative includes derivatives such as PEG-groups.

The terms peptide and proteins are used interchangeable and is not meant as indications or limitations as to size or function of the sequences.

DESCRIPTION OF THE INVENTION

The Met-Ap from *E. coli* has a substrate defining pocket (as part of active site) essentially, but probably not exclusively, defined by the amino acids Tyr 168, Met 206 and Gln 233. Mutating these positions extends the enzymes substrate specificity. The novel *E. coli* aminopeptidases described in the present invention extends the applicability of the Methionine aminopeptidases to be useful for removing the initiating methionine from almost any type of protein or peptide regardless of the amino acid sequence downstream of the methionine (P1' position). Hence, the initiator methionine can be removed from all initiator methionine containing peptides or proteins to produce initiator methionine-free peptides or proteins.

The *E. coli* Methionine aminopeptidase gene was cloned and mutant versions have been created using site directed mutagenesis.

The mutants were expressed in *E. coli* and the resulting enzymes were purified by conventional His-tag system. The enzyme can also be tagged by for example the FLAG-system or tagged and purified by other technologies as described in WO 03042249. Catalytic activity was monitored using initiator Met containing hIL-21 as a substrate.

In principle, the invention is generally applicable to any peptide. The invention is demonstrated as being useful for cleavage of the initiator methionine for peptides such as hIL-21. hIL-21 is a model system for P1' position being a Gln. IL-21 is described in WO00/53761 and is described as being effective in the treatment of cancer and viral infection among others. IL-20 is described in WO9927103. hGH refers to human Growth Hormone. Both are model systems for other amino acids in P1' position.

In an aspect the invention provides *E. coli* aminopeptidease variants which are mutated in the active site having extended substrate specificity the P1' position relative to the wild type.

In an aspect the invention provides the *E. coli* methionine aminopeptidase variants as described above which extend the substrate specificity in P1' position to include Asn, Leu, Ile, Phe, His, Gln or Trp as well as the amino acids allowed in position P1' by the wild type.

In an aspect the invention provides *E. coli* methionine aminopeptidases as described above, wherein the residues in positions 168, 206 or 233 has been amended into a sequence different from Y168 and/or M206 and/or Q233.

In an aspect the invention provides *E. coli* methionine aminopeptidases as described above, comprising amendments of the amino acid in position 168.

In an aspect the invention provides *E. coli* methionine aminopeptidases as described above comprising amendment in position 206.

In an aspect the invention provides *E. coli* methionine aminopeptidases as described above comprising amendment in position 233.

In an aspect the invention provides *E. coli* methionine aminopeptidases as described above, comprising amendments in position 206 and 233.

In an aspect the invention provides *E. coli* methionine aminopeptidases as described above comprising amendments in position 168 and 206.

In an aspect the invention provides *E. coli* methionine aminopeptidases as described above comprising amendments in position 168 and 233.

In an aspect the invention provides *E. coli* methionine aminopeptidase as described above, comprising amendments in positions 168, 206 and 233.

In an aspect the invention provides *E. coli* methionine aminopeptidases as described above, wherein the amendments comprises exchange of wildtype amino acid into Gly, Ala, Ser, Thr, Asn or Asp.

In an aspect the invention provides *E. coli* methionine aminopeptidases as described above, wherein the amendments comprises Ala and/or Gly.

In an aspect the invention provides *E. coli* methionine aminopeptidases as described above, wherein the amendments comprises Ala.

In an aspect the invention provides *E. coli* methionine aminopeptidase as described above, wherein position 168 is Ala.

In an aspect the invention provides *E. coli* methionine aminopeptidase as described above, wherein position 206 is Ala.

In an aspect the invention provides *E. coli* methionine aminopeptidase as described above, wherein position 233 is Ala.

The invention thus provides the methionine aminopeptidase enzyme having the following sequence (also described as seq. id. no. 1)

MAISIKTPEDIEKMRVAGRLAAEVLEMIEPYVKPGVSTGELDRICNDYIV

NEQHAVSACLGYHGYPKSVCISINEVVCHGIPDDAKLLKDGDIVNIDVTV

IKDGFHGDTSKMFIVGKPTIMGERLCRITQESLYLALRMVKPGINLREIG

AAIQKFVEAEGFSVVRE$X_a$ CGHGIGRGFHEEPQVLHYDSRETNVVLKPG

MTFTIEP$X_b$ VNAGKKEIRTMKDGWTVKTKDRSLSA$X_c$ YEHTIVVTDNG

CEILTLRKDDTIPAIISHDE, wherein $X_a$, $X_b$ and $X_c$ are variable amino acids, and wherein $X_a$, $X_b$ and $X_c$ are not simultaneously Tyr, Met and Gln respectively. In an aspect of the invention one or more of $X_a$, $X_b$ and $X_c$ are exchanged from the wild type amino acid into Gly, Ala, Ser, Thr, Asn or Asp. In an aspect of the invention $X_a$, $X_b$ and $X_c$ are exchanged from the wild type amino acid into Gly or Ala. In an aspect of the invention $X_a$, $X_b$ and $X_c$ are exchanged from the wild type amino acid into Ala.

The present invention thus provides substitution Y168 to Ala (Y168A) (Seq. id no. 9)

MAISIKTPEDIEKMRVAGRLAAEVLEMIEPYVKPGVSTGELDRICNDYIV

NEQHAVSACLGYHGYPKSVCISINEVVCHGIPDDAKLLKDGDIVNIDVTV

IKDGFHGDTSKMFIVGKPTIMGERLCRITQESLYLALRMVKPGINLREIG

AAIQKFVEAEGFSVVREACGHGIGRGFHEEPQVLHYDSRETNVVLKPGMT

FTIEPMVNAGKKEIRTMKDGWTVKTKDRSLSAQYEHTIVVTDNGCEILTL

RKDDTIPAIISHDE and the corresponding DNA encoding the above as seq. id. no. 8;

The present invention thus provides substitution Met 206 to Ala (M206A) (Seq. id no. 3)

MAISIKTPEDIEKMRVAGRLAAEVLEMIEPYVKPGVSTGELDRICNDYIV

NEQHAVSACLGYHGYPKSVCISINEVVCHGIPDDAKLLKDGDIVNIDVTV

IKDGFHGDTSKMFIVGKPTIMGERLCRITQESLYLALRMVKPGINLREIG

AAIQKFVEAEGFSVVREXCGHGIGRGFHEEPQVLHYDSRETNVVLKPGMT

FTIEPAVNAGKKEIRTMKDGWTVKTKDRSLSAQYEHTIVVTDNGCEILTL

RKDDTIPAIISHDE, which extends the enzymes substrate specificity to allow the following amino acids: Asn, Leu, Ile and Phe in the P1' position.

The present invention also provides substituting Gln 233 to Ala (Q233A) (Seq. id. No.5)

MAISIKTPEDIEKMRVAGRLAAEVLEMIEPYVKPGVSTGELDRICNDYIV

NEQHAVSACLGYHGYPKSVCISINEVVCHGIPDDAKLLKDGDIVNIDVTV

IKDGFHGDTSKMFIVGKPTIMGERLCRITQESLYLALRMVKPGINLREIG

AAIQKFVEAEGFSVVREXCGHGIGRGFHEEPQVLHYDSRETNVVLKPGMT

FTIEPMVNAGKKEIRTMKDGWTVKTKDRSLSAAYEHTIVVTDNGCEILTL

RKDDTIPAIISHDE, or both Met 206 and Gln 233 into Ala (M206A Q233A) (Seq. id no. 7):

MAISIKTPEDIEKMRVAGRLAAEVLEMIEPYVKPGVSTGELDRICNDYIV

NEQHAVSACLGYHGYPKSVCISINEVVCHGIPDDAKLLKDGDIVNIDVTV

IKDGFHGDTSKMFIVGKPTIMGERLCRITQESLYLALRMVKPGINLREIG

AAIQKFVEAEGFSVVREXCGHGIGRGFHEEPQVLHYDSRETNVVLKPGMT

FTIEPAVNAGKKEIRTMKDGWTVKTKDRSLSAAYEHTIVVTDNGCEILTL

RKDDTIPAIISHDE, which further allow the P1' amino acids to be His, Gln and Trp.

In aspects of the invention position 168 is amended into Gly (Y168G) or Ala (Y168A) or Asn (Y168N). Aspects of the invention are wherein amino acid 206 is an Ala (M206A) or a Gly (M206G) or Asn (M206N), and/or wherein amino acid 233 is an Ala (Q233A) or a Gly (Q233G) or Asn (Q233N). Aspects of the invention comprise the combination of two or three amendments according to the below, —wherein the wild-type combination of (Y168 M206 233Q) is not within the invention.

| Position 168 | Position 206 | Position 233 |
|---|---|---|
| A/G/N/Y | A/G/N/M | A/G/N/Q |

Accordingly, aspects of the invention are wherein position 206 and position 233 are both Ala (M206A Q233A) or Gly or Asn, or combinations thereof: (M206G Q233A), (M206G Q233G), (M206A Q233G), (M206N Q233A), (M206N Q233N), (M206A Q233N). Aspects of the invention are wherein position 168 is amended according to the below:

| Position 168 | Position 206 | Position 233 |
|---|---|---|
| A/G/N | A | Q |
| A/G/N | G | Q |
| A/G/N | N | Q |
| A/G/N | M | A |
| A/G/N | M | G |
| A/G/N | M | N |
| A/G/N | A | A |
| A/G/N | G | A |
| A/G/N | N | A |
| A/G/N | A | G |
| A/G/N | A | N |
| A/G/N | N | G |
| A/G/N | N | N |
| A/G/N | G | G |
| A/G/N | G | N |

Aspects of the invention are wherein at least one of the amended positions are amended into an Ala.

Aspects of the invention are the following mutants: (Y168G M206A), (Y168G M206A 233A), (Y168G M206N), (Y168G M206N 233A), (Y168A M206A 233A), (Y168A M206A), (Y168A M206N), (Y168A M206N 233A) and (M206A Q233A);

The invention thus provides a novel enzymes capable of cleaving a peptide containing an initiating methionine followed by a Asn, Leu, Ile, Phe, His, Gln or Trp in the P1' position as well as the amino acids allowed by the wild type *E. coli* aminopeptidase. Wildtype *E. coli* methionine aminopeptidase allows the P1' to be any of the following amino acids: Gly, Ala, Ser, Thr, Pro, Val or Cys.

The invention thus also provides recombinant DNA molecules encoding the sequence above. The DNA sequences are disclosed in Seq. id. no. 2, 4 and 6. The invention also provides specifically the DNA encoding the sequences for the mutants M206A, Q233A or M206A Q233A) above.

In the present invention the mutant Methionine aminopeptidases are expressed in *E. coli*, but in principle the host cells could be of other prokaryotic origin or eukaryotic origin such as *Saccharomyces cerevisiae, Schizosaccharomyces pombe, Pichia pastoris* etc. or for example mammalian cells.

The invention thus provides host cells transformed by the recombinant DNA molecule of above.

Removal of initiator methionine by methionine aminopeptidase may be performed in vitro following methionine aminopeptidase expression in, and purification from, prokaryotic or eukaryotic cells. This procedure is demonstrated below. Alternatively removal of initiator methionine may take place in vivo either in cells expressing a di-cistronic plasmid or in cells co-expressing plasmids carrying the methionine aminopeptidase and the substrate peptide or protein. In vivo initiator methionine processing may also be performed in cells where the genes encoding the methionine aminopeptidase and the peptide or protein to be processed have been integrated into the genome.

Experiments have been performed which provides a set of optimum conditions for the reaction: The optimal temperature for the reaction was determined to be between 15 and 24 degrees Celsius. Typically the reaction was hereafter performed at 18 degrees Celsius.

The concentration of $ZnCl_2$ was determined to be optimal at around 7.5 μM and NaCl concentration was found optimal around 100 mM and acceptable under 130 mM.

After cleavage of the initiator methionine separation of the product from the starting material can be achieved by exploiting the different biophysical properties of the two peptides.

In an embodiment of the invention the peptide is hIL-21, which after removal of the initial methionine contains a Gln in the N-terminal. Treatment with Qcyclase forms a pyroglutamine (pGlu). Due to cyclic amid formation the products net change is negative relative to the Methionine containing peptide. The difference in charge affects the eluation on a cation exchange column, due to Methionine containing peptide having a stronger binding to the cation resin. Further, in non-cyclised hIL-21 the N-terminal positioned Gln residue will have the ability to form a hydrogen bond between the side chain amide oxygen and the charged N-terminal backbone amine and thereby masking the charge at the N-terminus. Met-hIL-21 will not possess the ability for a similar charge masking and will therefore bind stronger to the cation exchange column than hIL-21.

In an embodiment of the invention, a method separation of protein mixtures between identical proteins starting with Met-Gln and Gln respectively is provided.

In a specific embodiment of the invention separation of Met-hIL-21 and hIL-21 is provided.

In another specific embodiment of the invention separation of Met-hIL-21 and hIL-21 and mutants thereof is provided.

EXAMPLES

Figure 1:
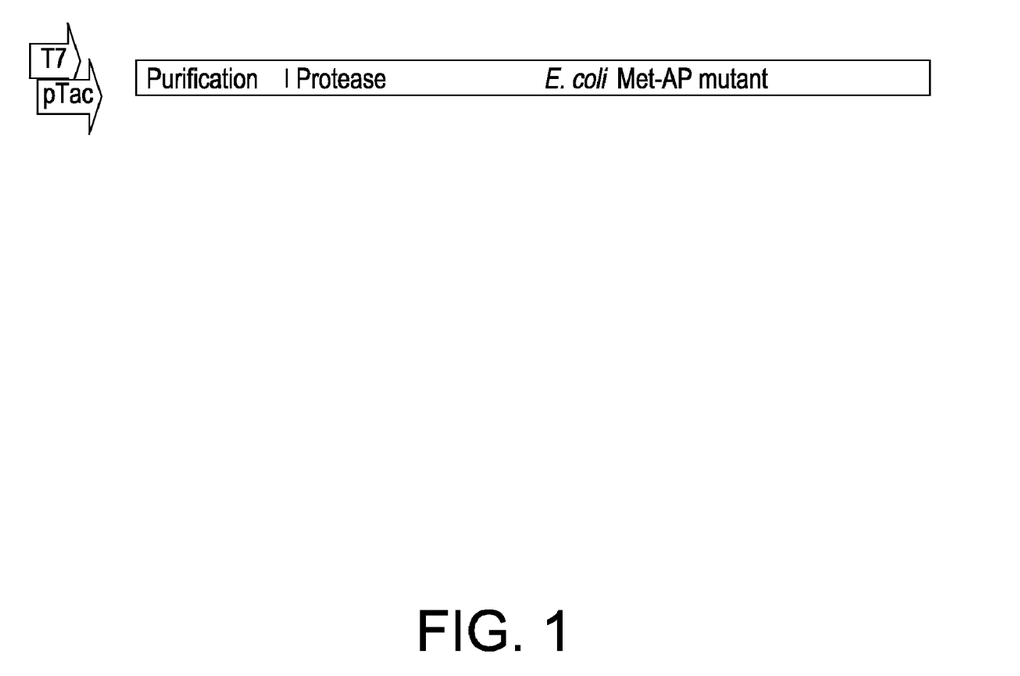
FIG. 1: Example of a *E. coli* Met-AP mutant expression construct layout. Purification indicates tag for purification purposes. Protease indicates protease cleavage site.
Figure 2:
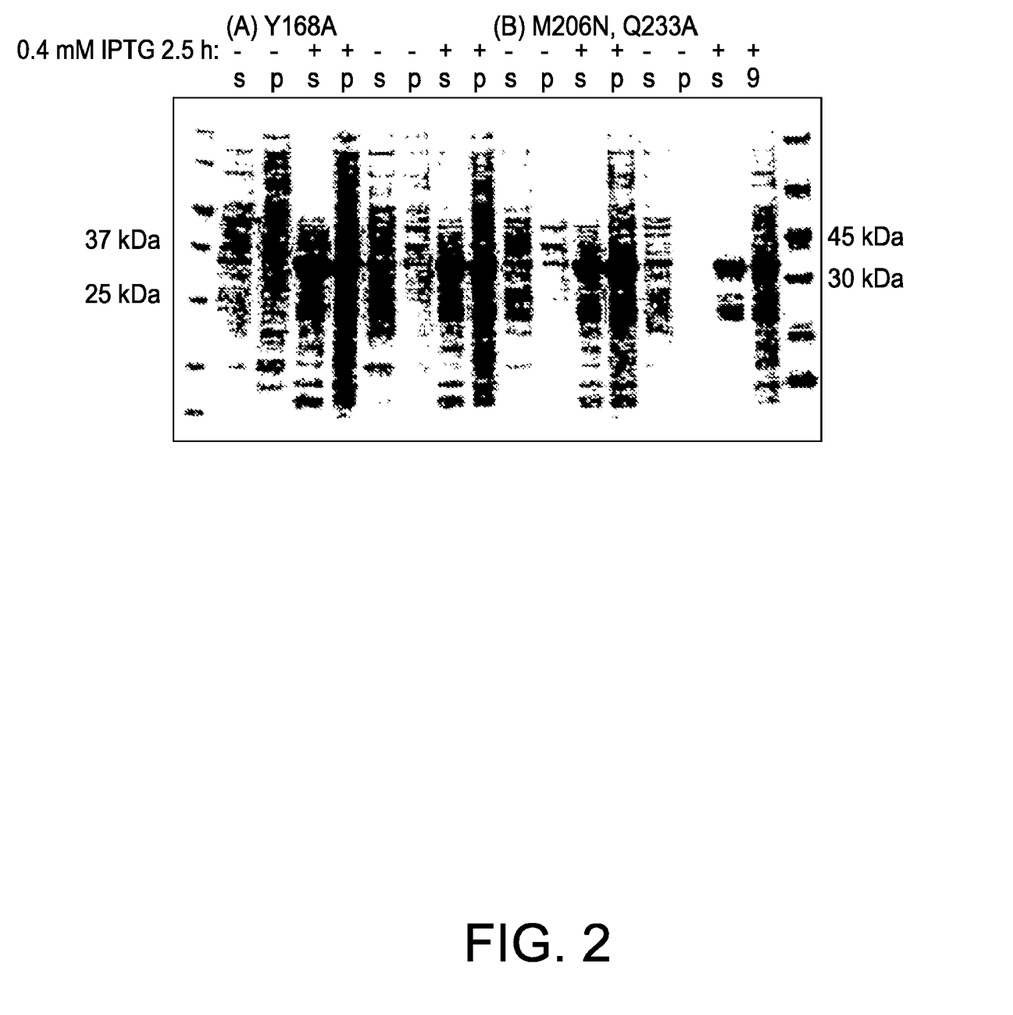
FIG. 2: Expression in e.g. *E. coli* of (A) NT1-Enterokinase-Met-AP Y168A or (B) NT1-Enterokinase-Met-AP Y168G, M206N, Q233A as indicated.

Various Met-AP expression constructs, as outlined in FIG. 1, have been created. NT1 (HHHNSWDHDINR) or hexa-His tag has been added to the various mutant forms of Met-AP for purification purposes. The purification tag may be removed using Factor Xa in some constructs or Enterokinase in others, or the purification tag may be left on the enzyme. mRNA expression was under the control of the T7 or the tac promoter. Constructs under the control of the T7 promoter were expressed in BL21(DE3) whereas constructs under the control of the tac promoter were expressed in BL21. Expression was induced by addition of IPTG to 0.4 mM to cultures (6 mL) grown to $OD_{600}$ 0.4 in LB-medium. Cells were harvested by centrifugation after 2.5 hours. Cell lysis was done by multiple freeze-thaw cycles and soluble or insoluble protein fractions were separated by centrifugation. Soluble or insoluble protein, before or after induction of expression, originating from equal amounts cells (measured by $OD_{600}$) were subjected to SDS-PAGE and subsequent colloidal blue staining (FIG. 2). Met-AP expression levels were estimated at ~250 mg/L after 2.5 h of induction in 6 mL cultures.

E. coli cells harvested from 1 L of culture expressing hexa-His-Met-AP M206A, Q233A were lysed using a cell disruptor, and the clarified lysate was applied on a $Ni^{2+}$-NTA superflow column. Elution with an imidazole gradient released the Met-AP fusion protein at approximately 200 mM imidazole. The enzyme was further purified and buffer exchanged (into storage/cleavage buffer) using size exclusion chromatography. The enzyme was analysed using SDS-PAGE, MALDI-MS and N-terminus sequencing—verifying the molecular mass and identity of the enzyme.

According to the procedure above NT1-Enterokinase-Met-AP mutants were prepared. Expression was under the control of the tac promoter. Addition of IPTG to the cultures induced primarily soluble expression of the Met-AP enzymes. The following mutants were prepared according to the above: (Y168G M206A), (Y168G M206A 233A), (Y168G M206N), (Y168G M206N 233A), (Y168A M206A 233A), (Y168A M206A), (Y168A M206N) and (Y168A M206N 233A)

Figure 4:
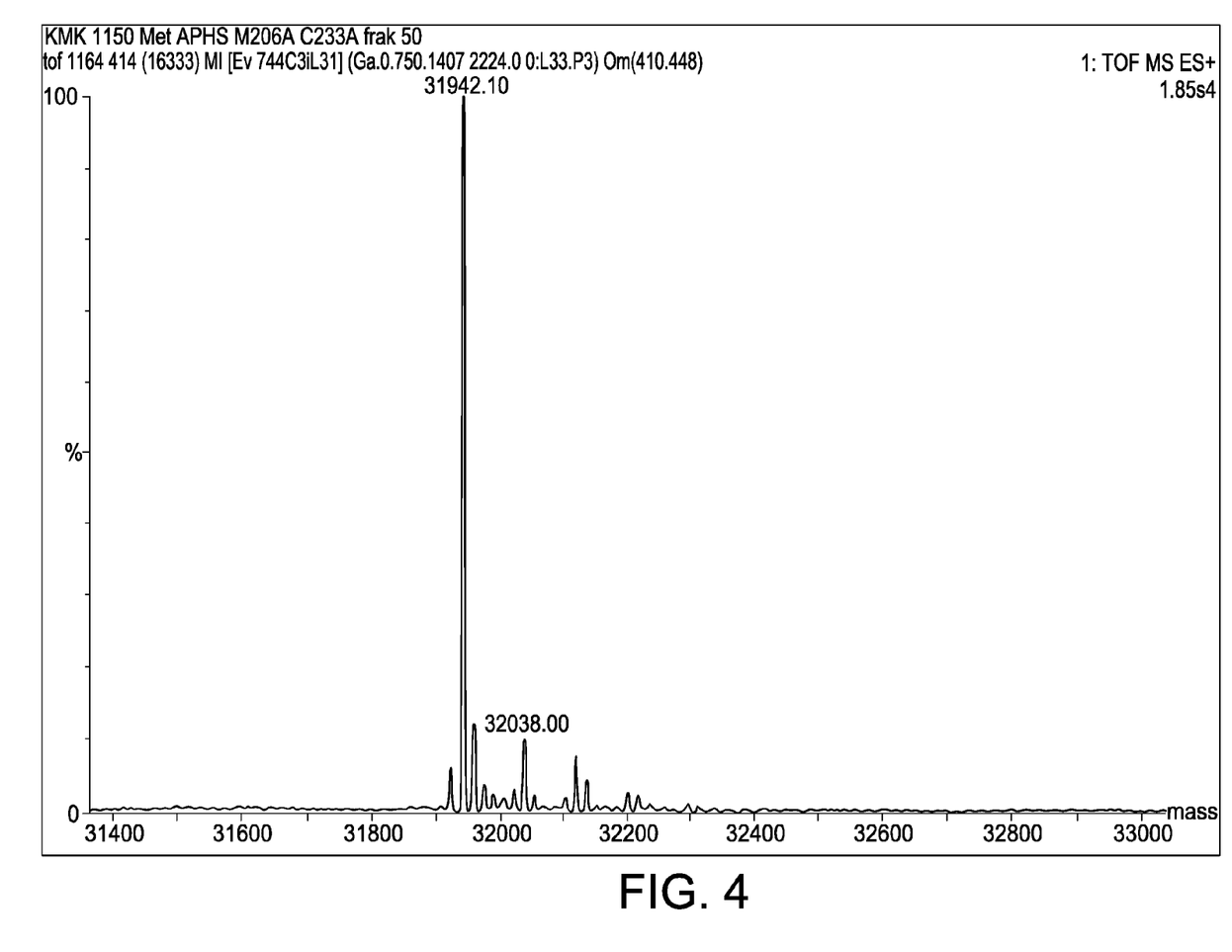
FIG. 4: Maldi-tof es mass spectrum of purified hexa-His-Xa-Met-AP M206A, Q233A.

Hexa-His-Xa-MetAP Q233A was affinity purified using $Ni^{2+}$-NTA superflow. Maldi-tof es mass spectrum of purified hexa-His-Xa-Met-AP M206A, Q233A shows that the correct enzymes were isolated. A mass of 32038.90 corresponds to Met-hexa-His-Xa-Met-AP M206A, Q233A and a mass of 31942.10 corresponds to hexa-His-Xa-Met-AP M206A, Q233A indicating that hexa-His-Xa-Met-AP M206A, Q233A was processed by WT Met-AP or hexa-His-Xa-Met-AP M206A, Q233A in vivo. The result is demonstrated in FIG. 4.

Figure 3:
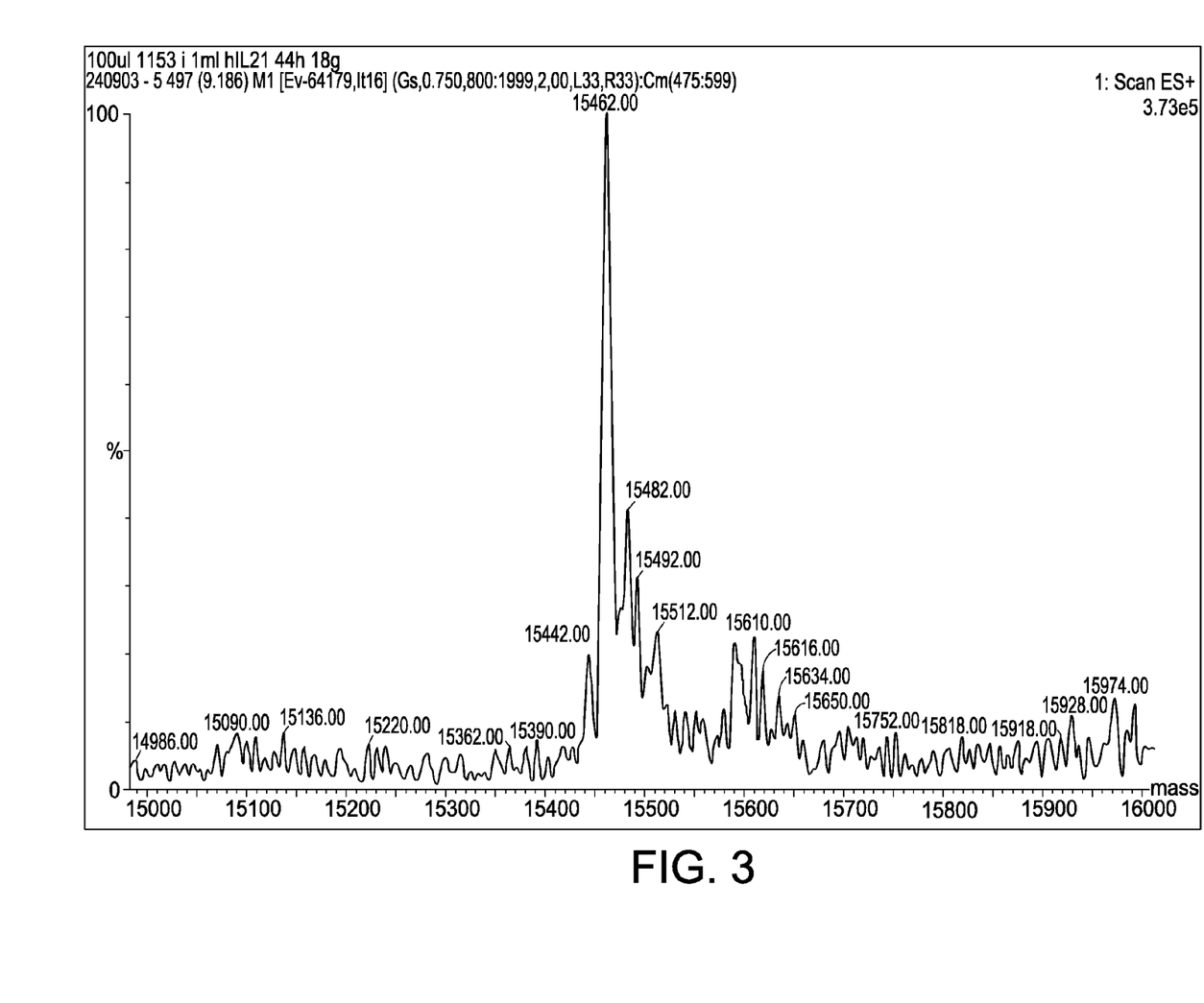
FIG. 3: hexa-His-Xa-Met-AP (M206A, Q233A) cleavage of Met-hIL-21

Addition of hexa-His-Xa-Met-AP M206A, Q233A to Met-hIL-21 at pH 7, 18° C. generated ~65% Met-free hIL-21. In 44 h. more than 90% cleavage of Met-hIL-21 could be observed (FIG. 3).

Another mutant prepared by this method was hexa-His-Xa-Met-AP Q233A;

Removal of Initiator Met from Met-IL21 by Met-AP (M206A, Q233A).

Purified Met-AP (M206A, Q233A) was used to remove the initiator Methionine from partly or fully purified Met-IL21. The cleavage was performed in a reaction buffer typically consisting of the following components: 2-100 mM $K_2SO_4$, 2-500 mM NaCl, 1-100 μM $ZnCl_2$ and 2-30 mM Hepes buffer pH 6-8. The cleavage was assayed by MALDI-TOF spectroscopy. The time of reaction was 2-66 hours. Using these condition removal of Methionine from Met-IL21 below detection limits of Met-IL21 could be performed.

Removal of Initiator Met from Met-IL21 by Met-AP (M206A).

Purified Met-AP (M206A) was used to remove the initiator Methionine from partly or fully purified Met-IL21. The cleavage was performed in a reaction buffer typically consisting of the following components: 2-100 mM $K_2SO_4$, 2-500 mM NaCl, 1-100 μM $ZnCl_2$ and 2-30 mM Hepes buffer pH 6-8. The cleavage was assayed by MALDI-TOF spectroscopy. The time of reaction was 2-66 hours. Using these condition removal of Methionine from Met-IL21 below detection limits of Met-IL21 could be performed.

Influence of Temperature on Removal of Initiator Met from Met-IL21 by Met-AP (M206A, Q233A).

Using the conditions and assay described in example 1 the temperature was varied between 4, 15, 24 and 30 degrees Celsius, respectively while the other parameters was fixed. The optimal temperature for the reaction was determined to be between 15 and 24 degrees Celsius. Typically the reaction was hereafter performed at 18 degrees Celsius.

Influence of $ZnCl_2$ Concentration on Removal of Initiator Met from Met-IL21 by Met-AP (M206A, Q233A).

Using the conditions and assay described in example 1 the $ZnCl_2$ concentration was varied between 7.5, 11 and 15 μM, respectively while the other parameters were fixed. The optimal $ZnCl_2$ concentration for the reaction was determined to be 7.5 μM. Typically, the reaction was hereafter performed at 7.5 μM $ZnCl_2$.

Influence of NaCl Concentration on Removal of Initiator Met from Met-IL21 by Met-AP (M206A, Q233A).

Using the conditions and assay described in example 1 the NaCl concentration was varied between 80, 130 and 180 mM, respectively while the other parameters were fixed. The maximum NaCl concentration tolerated for the reaction to run was determined to be 130 mM. Typically the reaction was hereafter performed at 100 mM NaCl.

Influence of the Addition of Q-Cyclase on Removal of Initiator Met from Met-IL21 by Met-AP (M206A, Q233A) and the Formation of Pyro-glutamine.

Using the conditions as described in examples above the effect of adding Q-cyclase to the reaction mixture was determined. Again MALDI-TOF was used for assaying the removal of Methionine and subsequently conversion of glutamine in position 1 in IL21 into pyro-glutamine. It was found that the addition of Q-cyclase to the reaction mixture did not negatively influence the removal of initiator Methionine from Met-IL21 and further the Q-cyclase was fully efficient in converting glutamine in position 1 in IL21 into pyro-glutamine under the reaction conditions described in the examples above.

Purification and Separation of Met-IL21, IL21 and Pyro-Glutamine IL-21 Using a Mono-S Column.

Figure 5:
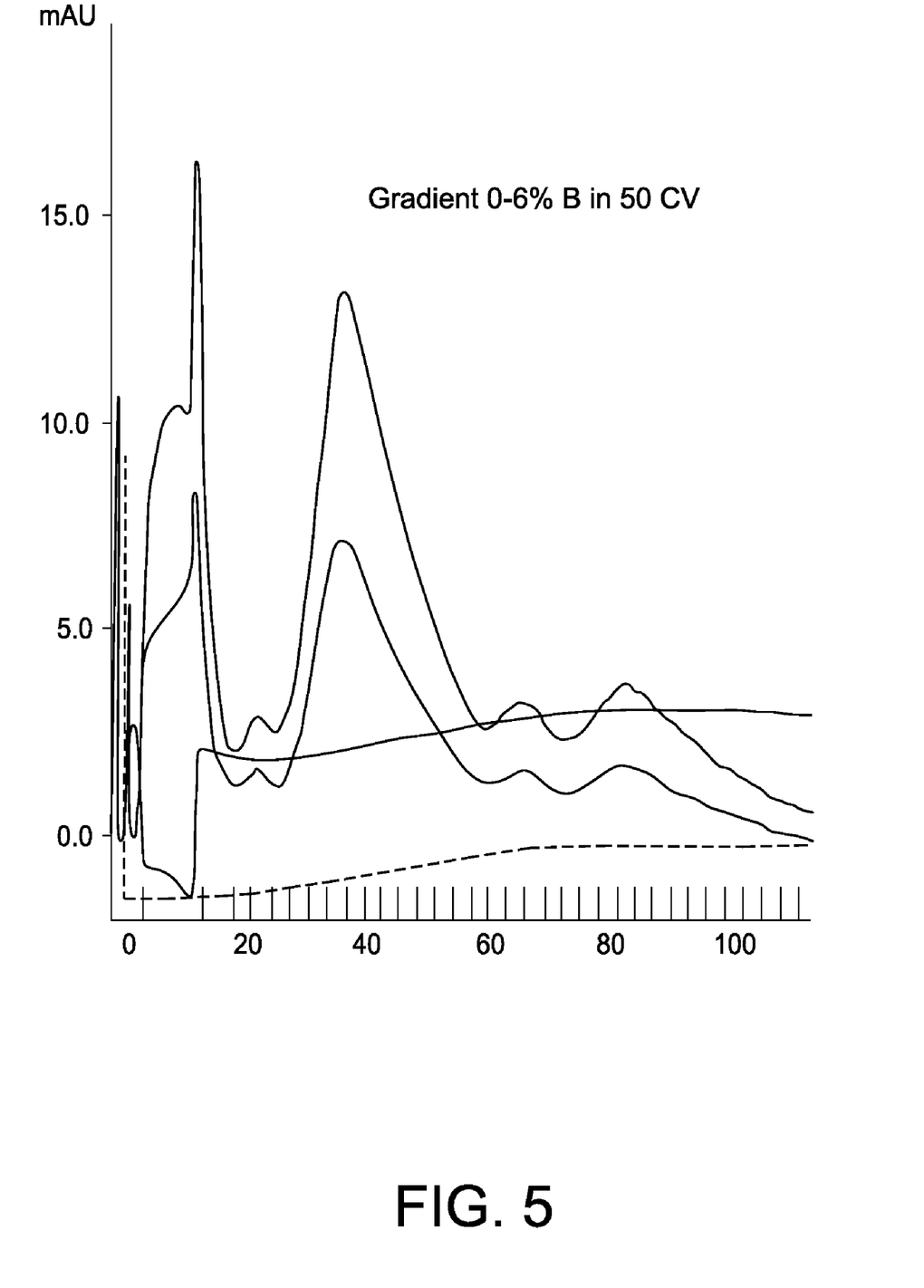
FIG. 5: Purification chromotogram of the separation of the three compounds Met-IL-21, IL-21 and pyroglutamine IL-21.

The different bio-physical properties between Met-IL21, IL21 and pyro-glutamine IL21 can be used for purification purposes/separation. Pyro-glutamine IL21 will due to the cyclized amid formation lack the normal protonation of the N-terminus. The (−1) charge difference between hIl-21 starting with pyro-glutamine and Met-IL21 can be used on a cation exchange column that will elute pyro-glutamine IL21 first (due to its lack of one positive charge) and subsequently Met-IL21 which displays a stronger binding to the cation resin. Further, in non-cyclized IL21 the N-terminally positioned glutamine will have the ability to form a hydrogen bond between the side chain amide oxygen and the charged N-terminal backbone amine, and thereby masking the charge at the N-terminus. Met-IL21 will not poses the ability for a similar charge masking and will therefore bind stronger to a cation exchange column than IL21. A mixture of Met-IL21, IL21 and pyro-glytamine IL21 including 300 mM NaCl and buffered at pH 6.5 was loaded on a Mono-S column. The A buffer consisted of 300 mM NaCl buffered at pH 6.5 and the B buffer 1 M NaCl buffered at pH 6.5. A linear gradient (performed on an AKTA system) from 0-20% B buffer was applied over 45 column volumes. The fractions was assayed as described under the Q-cyclase example above. Using the above described gradient, efficient separation of Met-IL21, IL21. pyro-glutamine IL21 was achieved. (FIG. 5)

Met-hGH

Purified Met-AP (M206A) is used to remove the initiator Methionine from partly or fully purified Met-hGH (human growth hormone) where the P1' is a Phe residue. The cleavage is performed in a reaction buffer typically consisting of the following components: 2-100 mM $K_2SO_4$, 2-500 mM NaCl, 1-100 µM $ZnCl_2$ and 2-30 mM Hepes buffer pH 6-8. The cleavage is assayed by MALDI-TOF spectroscopy. The time of reaction is 2-66 hours. Using these conditions partly or full removal of Methionine from Met-hGH is demonstrated.

Met-hGH

Purified Met-AP (M206A, Q233A) is used to remove the initiator Methionine from partly or fully purified Met-hGH (human growth hormone) where the P1' is a Phe residue. The cleavage is performed in a reaction buffer typically consisting of the following components: 2-100 mM $K_2SO_4$, 2-500 mM NaCl, 1-100 µM $ZnCl_2$ and 2-30 mM Hepes buffer pH 6-8. The cleavage is assayed by MALDI-TOF spectroscopy. The time of reaction is 2-66 hours. Using these conditions partly or full removal of Methionine from Met-hGH is achieved.

Met-IL-20

Purified Met-AP (M206A) is used to remove the initiator Methionine from partly or fully purified Met-IL-20 where the P1' is a Leu residue. The cleavage is performed in a reaction buffer typically consisting of the following components: 2-100 mM $K_2SO_4$, 2-500 mM NaCl, 1-100 µM $ZnCl_2$ and 2-30 mM Hepes buffer pH 6-8. The cleavage is assayed by MALDI-TOF spectroscopy. The time of reaction is 2-66 hours. Using these conditions partly or full removal of Methionine from Met-IL-20 is demonstrated.

Met-IL-20

Purified Met-AP (M206A, Q233A) is used to remove the initiator Methionine from partly or fully purified Met-IL-20 where the P1' is a Leu residue. The cleavage is performed in a reaction buffer typically consisting of the following components: 2-100 mM $K_2SO_4$, 2-500 µM NaCl, 1-100 µM $ZnCl_2$ and 2-30 mM Hepes buffer pH 6-8. The cleavage is assayed by MALDI-TOF spectroscopy. The time of reaction is 2-66 hours. Using these conditions partly or full removal of Methionine from Met-IL-20 is demonstrated.

The invention claimed is:

1. A method for purifying a product peptide having Gln in the N-terminus of its amino acid sequence from a substrate peptide comprising the Gln residue and an initiator Met residue in the N-terminus of its amino acid sequence comprising applying Qcyclase to the substrate peptide and purifying the product peptide by using the charge difference between the product peptide and substrate.

2. The method of claim 1, comprising purification of the substrate on a cation exchange column.

3. The method of claim 1, wherein the product peptide is interleukin-21 (IL-21).

4. The method of claim 2, wherein the product peptide is IL-21.

* * * * *

UNITED STATES PATENT AND TRADEMARK OFFICE
CERTIFICATE OF CORRECTION

| | | |
|---|---|---|
| PATENT NO. | : 7,662,935 B2 | Page 1 of 1 |
| APPLICATION NO. | : 12/471884 | |
| DATED | : February 16, 2010 | |
| INVENTOR(S) | : Nørby et al. | |

It is certified that error appears in the above-identified patent and that said Letters Patent is hereby corrected as shown below:

In column 21, line 16, claim 1, please delete "Gin" and insert --Gln--.

Signed and Sealed this

Eleventh Day of May, 2010

David J. Kappos
*Director of the United States Patent and Trademark Office*

SEQUENCE LISTING

```
<160> NUMBER OF SEQ ID NOS: 9

<210> SEQ ID NO 1
<211> LENGTH: 264
<212> TYPE: PRT
<213> ORGANISM: Escherichia coli
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (233)..(233)
<223> OTHER INFORMATION: Xaa can be any naturally occurring amino acid

<400> SEQUENCE: 1

Met Ala Ile Ser Ile Lys Thr Pro Glu Asp Ile Glu Lys Met Arg Val
1               5                   10                  15

Ala Gly Arg Leu Ala Ala Glu Val Leu Glu Met Ile Glu Pro Tyr Val
            20                  25                  30

Lys Pro Gly Val Ser Thr Gly Glu Leu Asp Arg Ile Cys Asn Asp Tyr
        35                  40                  45

Ile Val Asn Glu Gln His Ala Val Ser Ala Cys Leu Gly Tyr His Gly
    50                  55                  60

Tyr Pro Lys Ser Val Cys Ile Ser Ile Asn Glu Val Val Cys His Gly
65                  70                  75                  80

Ile Pro Asp Asp Ala Lys Leu Leu Lys Asp Gly Asp Ile Val Asn Ile
                85                  90                  95

Asp Val Thr Val Ile Lys Asp Gly Phe His Gly Asp Thr Ser Lys Met
            100                 105                 110

Phe Ile Val Gly Lys Pro Thr Ile Met Gly Glu Arg Leu Cys Arg Ile
        115                 120                 125

Thr Gln Glu Ser Leu Tyr Leu Ala Leu Arg Met Val Lys Pro Gly Ile
    130                 135                 140
```

Asn Leu Arg Glu Ile Gly Ala Ala Ile Gln Lys Phe Val Ala Glu
145                 150                 155                 160

Gly Phe Ser Val Val Arg Glu Xaa Cys Gly His Gly Ile Gly Arg Gly
                165                 170                 175

Phe His Glu Glu Pro Gln Val Leu His Tyr Asp Ser Arg Glu Thr Asn
                180                 185                 190

Val Val Leu Lys Pro Gly Met Thr Phe Thr Ile Glu Pro Xaa Val Asn
                195                 200                 205

Ala Gly Lys Lys Glu Ile Arg Thr Met Lys Asp Gly Trp Thr Val Lys
                210                 215                 220

Thr Lys Asp Arg Ser Leu Ser Ala Xaa Tyr Glu His Thr Ile Val Val
225                 230                 235                 240

Thr Asp Asn Gly Cys Glu Ile Leu Thr Leu Arg Lys Asp Asp Thr Ile
                245                 250                 255

Pro Ala Ile Ile Ser His Asp Glu
                260

<210> SEQ ID NO 2
<211> LENGTH: 792
<212> TYPE: DNA
<213> ORGANISM: Escherichia coli

<400> SEQUENCE: 2
atggctatct caatcaagac cccagaagat atcgaaaaaa tgcgcgtcgc tggccgactg      60
gctgccgaag tgctggagat gatcgaaccg tatgttaaac cgggcgtcag caccggcgag     120
ctggatcgca tctgtaatga ttacattgtt aatgaacaac acgcggtttc tgcctgcctc     180
ggctatcacg gctatccgaa atccgtttgc atctctatta tgaagtggt gtgccacggt      240 atcccggacg atgctaagct gctgaaagat ggcgatatcg ttaacattga tgtcaccgta     300
atcaaagatg gtttccacgg cgataccctc gaaaatgttta cgtcggtaa gccgaccatc     360 atgggcgaac gtctgtgccg catcacgcaa gaaagcctgt acctggcgct acgcatggta     420
aaaccaggca ttaatctgcg cgaaatcggt gcggcgattc agaaatttgt cgaagcagaa     480
ggcttctccg tcgttcgtga atattgcgga cacggtattg gtcgcggctt ccatgaagaa     540
ccgcaggtgc tgcactatga ctcccgtgaa accaacgtcg tactgaaacc tgggatgacg     600
ttcaccatcg agccagcggt caacgcgggt aaaaaagaga tccgcaccat gaaagatggc     660
tggacggtaa aaaccaaaga tcgcagcttg tctgcacagt atgagcatac tattgtggtg     720
actgataacg gctgcgaaat tctgacgcta cgcaaggatg acaccatccc ggcgataatc     780
tcgcacgacg aa                                                         792

<210> SEQ ID NO 3
<211> LENGTH: 264
<212> TYPE: PRT
<213> ORGANISM: Escherichia coli

<400> SEQUENCE: 3

Met Ala Ile Ser Ile Lys Thr Pro Glu Asp Ile Glu Lys Met Arg Val
1               5                   10                  15

Ala Gly Arg Leu Ala Ala Glu Val Leu Glu Met Ile Glu Pro Tyr Val
                20                  25                  30

Lys Pro Gly Val Ser Thr Gly Glu Leu Asp Arg Ile Cys Asn Asp Tyr
                35                  40                  45

Ile Val Asn Glu Gln His Ala Val Ser Ala Cys Leu Gly Tyr His Gly

```
                50                  55                  60
Tyr Pro Lys Ser Val Cys Ile Ser Ile Asn Glu Val Val Cys His Gly
 65                  70                  75                  80

Ile Pro Asp Asp Ala Lys Leu Leu Lys Asp Gly Asp Ile Val Asn Ile
                 85                  90                  95

Asp Val Thr Val Ile Lys Asp Gly Phe His Gly Asp Thr Ser Lys Met
            100                 105                 110

Phe Ile Val Gly Lys Pro Thr Ile Met Gly Glu Arg Leu Cys Arg Ile
        115                 120                 125

Thr Gln Glu Ser Leu Tyr Leu Ala Leu Arg Met Val Lys Pro Gly Ile
    130                 135                 140

Asn Leu Arg Glu Ile Gly Ala Ala Ile Gln Lys Phe Val Glu Ala Glu
145                 150                 155                 160

Gly Phe Ser Val Val Arg Glu Tyr Cys Gly His Gly Ile Gly Arg Gly
                165                 170                 175

Phe His Glu Glu Pro Gln Val Leu His Tyr Asp Ser Arg Glu Thr Asn
            180                 185                 190

Val Val Leu Lys Pro Gly Met Thr Phe Thr Ile Glu Pro Ala Val Asn
        195                 200                 205

Ala Gly Lys Lys Glu Ile Arg Thr Met Lys Asp Gly Trp Thr Val Lys
    210                 215                 220

Thr Lys Asp Arg Ser Leu Ser Ala Gln Tyr Glu His Thr Ile Val Val
225                 230                 235                 240

Thr Asp Asn Gly Cys Glu Ile Leu Thr Leu Arg Lys Asp Asp Thr Ile
                245                 250                 255

Pro Ala Ile Ile Ser His Asp Glu
            260

<210> SEQ ID NO 4
<211> LENGTH: 792
<212> TYPE: DNA
<213> ORGANISM: Escherichia coli

<400> SEQUENCE: 4
atggctatct caatcaagac cccagaagat atcgaaaaaa tgcgcgtcgc tggccgactg        60
gctgccgaag tgctggagat gatcgaaccg tatgttaaac cgggcgtcag caccggcgag       120
ctggatcgca tctgtaatga ttacattgtt aatgaacaac acgcggtttc tgcctgcctc       180
ggctatcacg ctatccgaa atccgtttgc atctctatta atgaagtggt gtgccacggt       240
atcccggacg atgctaagct gctgaaagat ggcgatatcg ttaacattga tgtcaccgta       300
atcaaagatg gtttccacgg cgatacctcg aaaatgttta cgtcggtaa gccgaccatc       360
atgggcgaac gtctgtgccg catcacgcaa gaaagcctgt acctggcgct acgcatggta       420
aaaccaggca ttaatctgcg cgaaatcggt gcggcgattc agaaatttgt cgaagcagaa       480
ggcttctccg tcgttcgtga atattgcgga cacggtattg gtcgcggctt ccatgaagaa       540
ccgcaggtgc tgcactatga ctcccgtgaa accaacgtcg tactgaaacc tgggatgacg       600
ttcaccatcg agccaatggt caacgcgggt aaaaaagaga tccgcaccat gaaagatggc       660
tggacggtaa aaaccaaaga tcgcagcttg tctgcagcgt atgagcatac tattgtggtg       720
actgataacg gctgcgaaat tctgacgcta cgcaaggatg acaccatccc ggcgataatc       780
tcgcacgacg aa                                                           792

<210> SEQ ID NO 5
```

```
<211> LENGTH: 264
<212> TYPE: PRT
<213> ORGANISM: Escherichia coli

<400> SEQUENCE: 5

Met Ala Ile Ser Ile Lys Thr Pro Glu Asp Ile Glu Lys Met Arg Val
1               5                   10                  15

Ala Gly Arg Leu Ala Ala Glu Val Leu Glu Met Ile Glu Pro Tyr Val
            20                  25                  30

Lys Pro Gly Val Ser Thr Gly Glu Leu Asp Arg Ile Cys Asn Asp Tyr
        35                  40                  45

Ile Val Asn Glu Gln His Ala Val Ser Ala Cys Leu Gly Tyr His Gly
50                  55                  60

Tyr Pro Lys Ser Val Cys Ile Ser Ile Asn Glu Val Val Cys His Gly
65                  70                  75                  80

Ile Pro Asp Asp Ala Lys Leu Leu Lys Asp Gly Asp Ile Val Asn Ile
                85                  90                  95

Asp Val Thr Val Ile Lys Asp Gly Phe His Gly Asp Thr Ser Lys Met
            100                 105                 110

Phe Ile Val Gly Lys Pro Thr Ile Met Gly Glu Arg Leu Cys Arg Ile
        115                 120                 125

Thr Gln Glu Ser Leu Tyr Leu Ala Leu Arg Met Val Lys Pro Gly Ile
130                 135                 140

Asn Leu Arg Glu Ile Gly Ala Ala Ile Gln Lys Phe Val Glu Ala Glu
145                 150                 155                 160

Gly Phe Ser Val Val Arg Glu Tyr Cys Gly His Gly Ile Gly Arg Gly
                165                 170                 175

Phe His Glu Glu Pro Gln Val Leu His Tyr Asp Ser Arg Glu Thr Asn
            180                 185                 190

Val Val Leu Lys Pro Gly Met Thr Phe Thr Ile Glu Pro Met Val Asn
        195                 200                 205

Ala Gly Lys Lys Glu Ile Arg Thr Met Lys Asp Gly Trp Thr Val Lys
210                 215                 220

Thr Lys Asp Arg Ser Leu Ser Ala Ala Tyr Glu His Thr Ile Val Val
225                 230                 235                 240

Thr Asp Asn Gly Cys Glu Ile Leu Thr Leu Arg Lys Asp Asp Thr Ile
                245                 250                 255

Pro Ala Ile Ile Ser His Asp Glu
            260

<210> SEQ ID NO 6
<211> LENGTH: 792
<212> TYPE: DNA
<213> ORGANISM: Escherichia coli

<400> SEQUENCE: 6
atggctatct caatcaagac cccagaagat atcgaaaaaa tgcgcgtcgc tggccgactg      60
gctgccgaag tgctggagat gatcgaaccg tatgttaaac cgggcgtcag caccggcgag     120
ctggatcgca tctgtaatga ttacattgtt aatgaacaac acgcggtttc tgcctgcctc     180
ggctatcacg gctatccgaa atccgtttgc atctctatta tgaagtggt gtgccacggt      240 atcccggacg atgctaagct gctgaaagat ggcgatatcg ttaacattga tgtcaccgta     300
atcaaagatg gtttccacgg cgataccctc gaaaatgttta tcgtcggtaa gccgaccatc     360
atgggcgaac gtctgtgccg catcacgcaa gaaagcctgt acctggcgct acgcatggta     420
```

```
aaaccaggca ttaatctgcg cgaaatcggt gcggcgattc agaaatttgt cgaagcagaa      480
ggcttctccg tcgttcgtga atattgcgga cacggtattg gtcgcggctt ccatgaagaa      540
ccgcaggtgc tgcactatga ctcccgtgaa accaacgtcg tactgaaacc tgggatgacg      600
ttcaccatcg agccagcggt caacgcgggt aaaaaagaga tccgcaccat gaaagatggc      660
tggacggtaa aaaccaaaga tcgcagcttg tctgcagcgt atgagcatac tattgtggtg      720
actgataacg gctgcgaaat tctgacgcta cgcaaggatg acaccatccc ggcgataatc      780
tcgcacgacg aa                                                         792
```

<210> SEQ ID NO 7
<211> LENGTH: 264
<212> TYPE: PRT
<213> ORGANISM: Escherichia coli

<400> SEQUENCE: 7

```
Met Ala Ile Ser Ile Lys Thr Pro Glu Asp Ile Glu Lys Met Arg Val
 1               5                  10                  15

Ala Gly Arg Leu Ala Ala Glu Val Leu Glu Met Ile Glu Pro Tyr Val
             20                  25                  30

Lys Pro Gly Val Ser Thr Gly Glu Leu Asp Arg Ile Cys Asn Asp Tyr
         35                  40                  45

Ile Val Asn Glu Gln His Ala Val Ser Ala Cys Leu Gly Tyr His Gly
     50                  55                  60

Tyr Pro Lys Ser Val Cys Ile Ser Ile Asn Glu Val Val Cys His Gly
 65                  70                  75                  80

Ile Pro Asp Asp Ala Lys Leu Leu Lys Asp Gly Asp Ile Val Asn Ile
                 85                  90                  95

Asp Val Thr Val Ile Lys Asp Gly Phe His Gly Asp Thr Ser Lys Met
            100                 105                 110

Phe Ile Val Gly Lys Pro Thr Ile Met Gly Glu Arg Leu Cys Arg Ile
        115                 120                 125

Thr Gln Glu Ser Leu Tyr Leu Ala Leu Arg Met Val Lys Pro Gly Ile
    130                 135                 140

Asn Leu Arg Glu Ile Gly Ala Ala Ile Gln Lys Phe Val Glu Ala Glu
145                 150                 155                 160

Gly Phe Ser Val Val Arg Glu Tyr Cys Gly His Gly Ile Gly Arg Gly
                165                 170                 175

Phe His Glu Glu Pro Gln Val Leu His Tyr Asp Ser Arg Glu Thr Asn
            180                 185                 190

Val Val Leu Lys Pro Gly Met Thr Phe Thr Ile Glu Pro Ala Val Asn
        195                 200                 205

Ala Gly Lys Lys Glu Ile Arg Thr Met Lys Asp Gly Trp Thr Val Lys
    210                 215                 220

Thr Lys Asp Arg Ser Leu Ser Ala Ala Tyr Glu His Thr Ile Val Val
225                 230                 235                 240

Thr Asp Asn Gly Cys Glu Ile Leu Thr Leu Arg Lys Asp Asp Thr Ile
                245                 250                 255

Pro Ala Ile Ile Ser His Asp Glu
            260
```

<210> SEQ ID NO 8
<211> LENGTH: 795
<212> TYPE: DNA
<213> ORGANISM: Escherichia coli

<400> SEQUENCE: 8

```
atggctatct caatcaagac cccagaagat atcgaaaaaa tgcgcgtcgc tggccgactg      60
gctgccgaag tgctggagat gatcgaaccg tatgttaaac cgggcgtcag caccggcgag     120
ctggatcgca tctgtaatga ttacattgtt aatgaacaac acgcgtttc tgcctgcctc      180
ggctatcacg gctatccgaa atccgtttgc atctctatta atgaagtggt gtgccacggt     240
atcccggacg atgctaagct gctgaaagat ggcgatatcg ttaacattga tgtcaccgta     300
atcaaagatg gtttccacgg cgataccteg aaaatgttta tcgtcggtaa gccgaccatc     360
atgggcgaac gtctgtgccg catcacgcaa gaaagcctgt acctggcgct acgcatggta     420
aaaccaggca ttaatctgcg cgaaatcggt gcggcgattc agaaatttgt cgaagcagaa     480
ggcttctccg tcgttcgtga agcgtgcgga cacggtattg tcgcggctt ccatgaagaa      540
ccgcaggtgc tgcactatga ctcccgtgaa accaacgtcg tactgaaacc tgggatgacg     600
ttcaccatcg agccaatggt caacgcgggt aaaaaagaga tccgcaccat gaaagatggc     660
tggacggtaa aaccaaagat cgcagcttg tctgcacaat atgagcatac tattgtggtg      720
actgataacg gctgcgaaat tctgacgcta cgcaaggatg acaccatccc ggcgataatc     780
tcgcacgacg aataa                                                     795
```

<210> SEQ ID NO 9
<211> LENGTH: 264
<212> TYPE: PRT
<213> ORGANISM: Escherichia coli

<400> SEQUENCE: 9

```
Met Ala Ile Ser Ile Lys Thr Pro Glu Asp Ile Glu Lys Met Arg Val
  1               5                  10                  15

Ala Gly Arg Leu Ala Ala Glu Val Leu Glu Met Ile Glu Pro Tyr Val
             20                  25                  30

Lys Pro Gly Val Ser Thr Gly Glu Leu Asp Arg Ile Cys Asn Asp Tyr
         35                  40                  45

Ile Val Asn Glu Gln His Ala Val Ser Ala Cys Leu Gly Tyr His Gly
     50                  55                  60

Tyr Pro Lys Ser Val Cys Ile Ser Ile Asn Glu Val Val Cys His Gly
 65                  70                  75                  80

Ile Pro Asp Asp Ala Lys Leu Leu Lys Asp Gly Asp Ile Val Asn Ile
                 85                  90                  95

Asp Val Thr Val Ile Lys Asp Gly Phe His Gly Asp Thr Ser Lys Met
            100                 105                 110

Phe Ile Val Gly Lys Pro Thr Ile Met Gly Glu Arg Leu Cys Arg Ile
        115                 120                 125

Thr Gln Glu Ser Leu Tyr Leu Ala Leu Arg Met Val Lys Pro Gly Ile
    130                 135                 140

Asn Leu Arg Glu Ile Gly Ala Ala Ile Gln Lys Phe Val Glu Ala Glu
145                 150                 155                 160

Gly Phe Ser Val Val Arg Glu Ala Cys Gly His Gly Ile Gly Arg Gly
                165                 170                 175

Phe His Glu Glu Pro Gln Val Leu His Tyr Asp Ser Arg Glu Thr Asn
            180                 185                 190

Val Val Leu Lys Pro Gly Met Thr Phe Thr Ile Glu Pro Met Val Asn
        195                 200                 205

Ala Gly Lys Lys Glu Ile Arg Thr Met Lys Asp Gly Trp Thr Val Lys
    210                 215                 220
```

-continued

```
Thr Lys Asp Arg Ser Leu Ser Ala Gln Tyr Glu His Thr Ile Val Val
225                 230                 235                 240

Thr Asp Asn Gly Cys Glu Ile Leu Thr Leu Arg Lys Asp Asp Thr Ile
                245                 250                 255

Pro Ala Ile Ile Ser His Asp Glu
                260
```